(12) United States Patent
Mathias et al.

(10) Patent No.: US 7,175,863 B1
(45) Date of Patent: Feb. 13, 2007

(54) METHOD OF ISOLATING STONE CELLS

(75) Inventors: Eckart Mathias, Goleta, CA (US); Joseph Campanale, Grover Beach, CA (US)

(73) Assignee: Den-Mat Corporation, Santa Maria, CA (US)

( * ) Notice: Subject to any disclaimer, the term of this patent is extended or adjusted under 35 U.S.C. 154(b) by 17 days.

(21) Appl. No.: 11/226,300

(22) Filed: Sep. 15, 2005

(51) Int. Cl.
*A61K 36/00* (2006.01)
*A61K 36/73* (2006.01)
(52) U.S. Cl. ...................... 424/777; 424/765
(58) Field of Classification Search .................. None
See application file for complete search history.

(56) References Cited

U.S. PATENT DOCUMENTS 1,527,523 A * 2/1925 Nitardy et al. ................ 424/58
3,860,726 A * 1/1975 Yamane ....................... 426/52

FOREIGN PATENT DOCUMENTS

JP          55102379 A          8/1980

* cited by examiner

*Primary Examiner*—Christopher R. Tate
*Assistant Examiner*—Melenie McCormick
(74) *Attorney, Agent, or Firm*—Crowell & Moring LLP; John W. Ryan; Thomas M. Haas

(57) ABSTRACT

A method for isolating stone cells and stone cell clusters from fruit. A puree of a stone cell-containing fruit is treated to provide a chemically induced separation of fibrous fruit pulp from stone cells and stone cell clusters. The method provides free-flowing stone cell powder for use as a mild abrasive.

18 Claims, No Drawings

METHOD OF ISOLATING STONE CELLS

BACKGROUND AND SUMMARY OF THE INVENTION

The invention relates to the isolation of stone cells from fruit.

Stone Cells are hard, granular materials predominantly found in pears and quince, as well as in other fruits such as sapota and guava. The stone cells cause the interior of these fruits to have a gritty texture. In botanical terminology, stone cells are referred to as sclereids, and are described as substantially lignified plant structures, which are part of the sclerenchyma of plant tissue.

There are several varieties of sclereids. Many are wiry, thin, elongated and often-branched structures, appearing somewhat like short veins. These vein-like sclereids provide physical strength to certain plant parts such as leaves, stems, fruits, etc. Other sclereids turn into lignified and dense shells such as those surrounding nuts, for example, walnut shells, almond shells, and pecan shells. The shells of pits of fleshy fruits, such as those of peaches, apricots, plums, and the like are also typical examples of sclereid material. Still others, specifically referred to as stone cells (and also known as brachysclereids), possess thick, lignified walls, and are granular, small, and dimensionally isodiametric. These sclereids are characterized by aspect ratios (length divided by width) in the range of 1 to 4, most typically about 1 to 2.

Stone cells are naturally present in the form of clusters of primary stone cells. The primary stone cells are generally very small particles (about 20 to 50 microns) and are usually agglomerated and lightly "fused" into isodiametric clusters 100 to 800 microns).

Stone cells are naturally attached to the fibrous pulp of the fruit. Stone cells are known to be indigestible and not pleasant to the palate when eaten. For those reasons, efforts have been made to remove stone cells from pulp so that the pulp may be added to fruit juice. For example, Japanese Patent Application No. 55102379, credited to Yamane, discloses a purely mechanical process for removing stone cells from pear juice. The method includes vigorously stirring the fruit juice, stopping the agitation, and allowing the stone cells to settle to the bottom of the tank. The juice product is then withdrawn from the upper portion of the tank, and the stone cells are taken out at the bottom.

Enzymes have also been proposed in order to aid in the removal of stone cells from fruit pulp. For example, U.S. Pat. No. 3,860,726, issued to Yamane, teaches using a peptidase to accelerate the separation of stone cells from pulp-like material. Yamane teaches use of the peptidase provides good chemical separation between the pulp and the stone cells and thus eliminates the need for common exfoliating and separating devices that cause a decrease in the viscosity of the puree. Yamane also discloses that a pectinase could be used for the same purpose; however, the pectinase undesirably causes a large decrease in the viscosity of the crude puree after the pectinase treatment. The objective of Yamane is to provide a puree that is stone cell-free, has a similar viscosity to the puree before stone cell removal, and as such is suitable for producing a fruit nectar. Accordingly, Yamane does not disclose any methods for treating the separated stone cells which are presumably just discarded as waste.

Stone cells are sometimes segregated (mostly unintentionally) during the processing of various plant materials, but such impure stone cells are heavily contaminated with pulp-like fibers, and thus the gritty and pulpy mass is treated as an undesirable by-product. Therefore, this "sludge" is merged into the regular waste stream of the process, e.g., in the processing of some fruits, and the making of paper products. Sometimes sclereids are separated on a large scale by a wet centrifugation method (e.g., a hydrocyclone) for improving a given product, and/or for semi-quantifying sclereid contents in fruit sauces, juices, and pulps in papermaking. Again, since there is no commercial use for these sclereids, they are disposed of as waste.

Until now, the only commercial uses of sclereid-derived products, known by the present inventors, are those arising from the grinding up of the hard sclereids of various nut shells to be used as abrading materials in "sand blasting" operations, and as an additive in some cosmetic compositions, such as exfoliating creams. Known techniques for "handling" unprocessed/unsegregated stone cells for viewing under the microscope do not actually isolate them. There are numerous descriptions in the botanical literature on how to visualize stone cells on a microscope stage (using lignin-specific stains), but these methods do not lead to an actual, deliberate isolation of the individual stone cells by separating the stone cells from its surrounding fleshy pulp.

The present inventors have discovered that isolated stone cells may find utility in commercial applications. Further the present inventors, have developed a method that provides virtually complete removal of the pulp from the stone cells. The inventive method provides free-flowing stone cells that slide past each other, allowing the dry mass of stone cells to flow smoothly like fine sand. The sand like stone cell material can be used in several applications.

SUMMARY OF THE INVENTION

One embodiment of the invention is a method for the isolation of stone cells from a fruit. A puree of a stone cell-containing fruit is provided. The fruit puree is treated to provide a chemically induced separation of the stone cells from the fruit pulp. The stone cells are washed to remove any remaining fruit pulp and the stone cells are dried.

Another embodiment of the invention is a method for the formation of a stone cell powder. A puree of a stone cell-containing fruit is provided. A base is provided to the fruit puree and the resulting puree is then heated to provide a chemically induced separation of stone cells and stone cell clusters from the pulp of the fruit. The stone cells and stone cell clusters are washed to remove any remaining fruit pulp and are dried to provide a free-flowing stone cell powder.

Another embodiment of the invention is a method for forming an exfoliating cream. A puree of a stone cell-containing fruit is provided. The fruit puree is treated to provide a chemically induced separation of the stone cells and stone cell clusters from the pulp of the fruit. The stone cells and stone cell clusters are washed to remove any remaining fruit pulp and are dried to provide a free-flowing stone cell powder. The stone cell powder is provided to a base cream.

DETAILED DESCRIPTION

One embodiment of the invention is a method for isolating stone cells from fruit. The starting material may be fresh or canned fruit or a "waste" stream from a stone cell separation process as described above. In a first step, a fruit puree is created. The puree may be contained in a vessel. The puree is then processed in order to cause a chemically induced separation between the fruit pulp and the stone cells. The separation results in the stone cells substantially settling at the bottom of the vessel and the pulpous material floating above the stone cells. The stone cells are then washed and dried. The method provides a stone cell powder that is free flowing and essentially pulp-free. Preferably, the isolated stone cells are predominantly clustered and substantially isodiametric.

The starting material may be fresh or canned fruit or a "waste" stream from a stone cell separation process as described above. In the case of isolating stone cells from pears, the fruit can be either used directly out of a can of pear-parts (substantially draining off the syrup first), or, the fresh fruit can be cored, peeled, and cut into small pieces to be cooked in water until soft enough for grinding into a puree. Since quince fruits are apparently not available in cans, the fresh fruit may be peeled, cored, cut and cooked until ready for pureeing. The fruit puree may be formed by any process such as mashing and pressing through a sieve or by using a food processor. In the case of the food processor, the screw that drives the fruit material through the sieve may need to be cleaned occasionally to remove course and fibrous material. Whichever process is used, the fleshy pulp of the fruit containing the stone cells is first broken up into a puree/sauce.

The puree made of the fruit of choice is further processed for separating the fibrous part of the flesh from the stone cells. As the goal of this invention is to remove substantially all of the attached fibers on the stone cells, the cells must be substantially stripped "chemically" by breaking the link between the two parts, but without significantly breaking up desirous stone cell clusters. Preferably, this is achieved by digesting the pulp in the presence of enzymes, followed by a simmering of the slurry near its boiling temperature at an elevated basicity (high pH). Any basic compound can be added to the fruit puree to provide the highly basic environment. Preferably, the basic compound is sodium hydroxide. Alternatively, the slurry may just be simmered near the boiling temperature at an elevated basicity (high pH) or at an elevated acidity (low pH). Alternatively, the slurry may simply be digested with the enzymes and no base heating. Optionally, after either the enzyme treatment or the enzyme-free treatment, the puree may be subjected to a period of high speed stirring using a dispensing blade, which results in tearing the small remaining pulp fibers off the stone cells and their clusters. A treatment process, which is chemically and/or physically too aggressive, may undesirably break up the stone cell clusters into the finer primary stone cells.

In the preferred embodiment that includes treating the puree with enzymes, any enzyme that aids in the separation of the fibrous part of the flesh from the stone cells may be used. Preferably, the enzymes are pectinases, which cleave carbohydrate bonds of the molecules that substantially make up the fibrous structures that are attached to the stone cells. Preferably these degradations are carried out in the presence of chemical buffers to provide a more stable and efficient acidity level during the enzyme digestion process. Especially applicable buffers are those that keep the pH of the medium in the acidic range of about 3 to 6. Most preferably, the buffer is chosen to hold a pH in the range of 4 to 5. An exemplary buffer system includes citric acid and diammonium citrate. The digestion is preferably run in the temperature range of about 40° C. to 65° C.; most preferably 50 to 60° C.

As opposed to Yamane's use of peptidases, which cleave peptide (amino acid) linkages of pulp material, pectinases cleave the macromolecules of pectin at carbohydrate linkages. The breakup of the pectin is necessary to preclude the formation of jelly-like mixtures, which prevent the stone cells from settling to the bottom of the reaction vessel.

The ultimate physical isolation of the stone cells from the fruit pulp can be carried out by any known method such as centrifugation, decantation, or a combination of both. Preferably, the separation process is a simple wash and decantation process. The pulpous liquid above the stone cells can simply be poured off while retaining the stone cells in the vessel. Fresh wash water, preferably de-ionized water, can then be poured over the stone cells followed by a second decantation. This process can be repeated until the stone cells are substantially free of fibrous material but two decantations is usually sufficient. Before the first decantation, fresh wash de-ionized water may be added to the stone cells if there is insufficient liquid to pour off the pulpous material. The isolated stone cells and stone cell clusters can then be washed with any hydrophilic solvent, such as isopropyl alcohol, to remove any remaining water. The stone cells can then be washed with acetone to aid in drying. The cells can then be dried in an oven at around 40° C. The separated pulp and juice from the fruit may be processed in any known manner to provide juice, nectar, sauce, or any other desired material.

If attached fibrous pulp remains, dry stone cells and their clusters are not free-flowing, because the pulp remaining on the surface of the stone cells entangles with the pulp of other stone cells, thus precluding the smooth sliding of the stone cells past each other. Stone cells devoid of attached pulp fibers slide past each other, allowing the dry mass of stone cells to flow smoothly like fine sand. The present invention provides isolated stone cells and stone cell clusters to form this sand-like powder.

The present invention provides isolated stone cells and stone cell clusters. The cells and clusters form a free-flowing powder. The stone cell powders can be used to impart mildly abrasive characteristics to a product, for soft "sand blasting", to improve sliding characteristics between two surfaces, and as an exfoliant in soaps, creams, and lotions and other soft-abrasive uses. The stone cell powders may also be used as a glued-on abrasive on substrates such as fabrics and films. One preferred application is in exfoliating creams as disclosed in co-assigned U.S. patent application Ser. No. 11/183,959, entitled "Exfoliating Cream", which is hereby incorporated by reference in its entirety.

EXAMPLES

Example 1

Formation of Pear Puree

The contents of two 1 gallon cans of pear halves (Bartlett) in light syrup (S&W Premium) was first drained of all the syrup, and the pear halves were then fed through a KitchenAid food processor (Model K5SSWW) with a puree-making attachment (Model FGA-2). After cleaning out the feeding screw, the pulp was processed a second time to further reduce the size of the pear chunks. The yield was about 2.7 kg of puree. The puree was then split into several portions, and poured into polyethylene containers for storage in a freezer.

Example 2

Formation of Quince Puree

Each of two fresh quinces were washed and peeled, and then cut into 4 equal wedges. The seed core of each wedge, and the stem and sepals, were removed. Each wedge was then cut into one-eighth-size wedges and then cut into about one-quarter inch pieces. The pieces were cooked in a Magnalite pot using just enough water to keep the pieces covered. The pieces were cooked under a simmering boil for six hours, after which the hot red water was decanted. After cooling to room temperature, the pieces were mashed to a medium size chunky sauce. The sauce was then processed into a fine puree using the KitchenAid processor as in Example 1.

Example 3

Isolation of Pear Stone Cells and Stone Cell Clusters

Into a 600 mL beaker (placed on a magnetic stirrer/hot-plate) was added 200 g of a pear puree (of about 18% solids and made by the same procedure described in Example 1). The puree was magnetically stirred and warmed to about 55° C., at which time a buffer system was added consisting of 0.70 g citric acid and 5.40 g diammonium citrate. To this mixture was added 1.0 g of enzyme blend Macer-8™ FJ and 1.0 g of enzyme blend Depol™ 670L, both from Biocatalysts Limited. The pH of the mixture was 4.5. The mixture was then digested with continuous stirring for 16.5 hours in the temperature range of 54–55° C. To the stirring mixture was then added 16.0 g of an 11.75% aqueous NaOH solution and 5.0 g of NaOH pellets. The pH rose to about 12. The mixture was then heated to 91° C. at which point another 3.5 g of NaOH pellets was added, to keep the pH in the range of 9 to 12. After another 25 minutes another 3.5 g of NaOH pellets was added, and the heating was continued for a total of about 3 hours. The resulting dark brown mixture was then cooled with the addition of de-ionized water, up to the capacity of the container, and this volume was then split into two approximately equal portions to facilitate the isolation of the stone cells by repeating the familiar settling/decantation routine. The routine was repeated until all the loose, free-floating pulp was discarded (two times). After the last decantation, the stone cells were washed first with isopropyl alcohol, followed by a wash with acetone, to facilitate their drying in an oven at 40° C. The dried sand-colored stone cells were free of pulp, and were free-flowing.

Example 4

Isolation of Quince Stone Cells and Stone Cell Clusters

Into a 600 mL beaker (placed on a magnetic stirrer/hot-plate) was added 141.5 g of a quince puree (made by the same procedure described in Example 2) and enough de-ionized water to fill to the 400 mL mark. The puree was magnetically stirred and warmed to 53.5° C., at which time a buffer system was added consisting of 33.77 g of sodium dihydrogen phosphate and 0.10 g of phosphoric acid. To this mixture was added 1.0 g of enzyme blend Macer8™ FJ and 1.0 g of enzyme blend Depol™ 670L, both from Biocatalysts Limited. The pH of the mixture was 4–5. The mixture was then digested with continuous stirring for 16.3 hours in the temperature range of 54–56° C. To the stirring mixture was then added incrementally a total of 16.8 g of NaOH pellets. The pH rose to about 12. The temperature of the mixture was then increased to 93° C. during a period of 2 hours. The resulting dark brown mixture was then cooled with the addition of de-ionized water to isolate the stone cells by repeating the familiar settling/decantation routine. After the last decantation, the stone cells were washed first with isopropyl alcohol, followed by a wash with acetone, to facilitate their drying in an oven at 40° C. The dried light brown stone cells were substantially free of pulp, and were free-flowing.

Example 5

Isolation of Pear Stone Cells and Stone Cell Clusters

Into a 1 L beaker (placed on a magnetic stirrer/hot-plate) was added 400 g of a pear puree (of about 18% solids and made by the same procedure described in Example 1). The puree was magnetically stirred and warmed to about 50° C., at which time a buffer system was added consisting of 0.40 g of benzoic acid and 0.94 g of sodium benzoate. This mixture was stirred for 2 hours, after which time was added 2.0 g of enzyme blend Macer8™ FJ and 2.0 g of enzyme blend Depol™ 670L, both from Biocatalysts Limited. The pH of the mixture was in the range of 4∴5. The mixture was then digested with continuous stirring for 16 hours in the temperature range of 53–58° C. To the stirring mixture was then added 25.0 g of a 50% aqueous NaOH solution. The pH rose to about 9. The temperature of the mixture was then heated to 92° C.; at which point another 10.0 g of a 50% aq. NaOH solution was added, to keep the pH in the range of 9 to 12. After an additional 30 minutes, another 10.0 g of a 50% aq. NaOH solution was added, and the heating was then continued for an additional 2.5 hours. The resulting dark brown mixture was then cooled and subjected to the known settling/decantation routine. The routine was repeated until all the loose, free-floating pulp was discarded. Prior to the last decantation, the stone cells were treated with a small amount of aqueous citric acid, which helped lighten the color of the stone cells. After the last decantation, the stone cells were washed first with isopropyl alcohol, followed by a wash with acetone, to facilitate their drying in an oven set at 40° C. The very light brown stone cells were free of pulp, and were free-flowing.

Example 6

Isolation of Pear Stone Cells and Stone Cell Clusters

Into a 1 L beaker (placed on a magnetic stirrer/hot-plate) was added 400 g of a pear puree (of about 18% solids and made by the same procedure described in Example 1). The puree was magnetically stirred and warmed to about 50° C., at which time a buffer system was added consisting of 67.53 g of sodium dihydrogen phosphate and 0.20 g of phosphoric acid. To this mixture was added 2.0 g of enzyme blend Macer8™ FJ and 2.0 g of enzyme blend Depol™ 670L, both from Biocatalysts Limited. The pH of the mixture was 4–5. The mixture was then digested with continuous stirring for 16 hours in the temperature range of 53–55° C. At the conclusion of the digestion, while increasing the temperature, to the stirring mixture was added, incrementally a total of 59.0 g of a 50% aqueous NaOH solution. The pH rose to 11–12. Additional base was added, in approximately 20 minutes interval, up to a total of 65.0 g of the 50% aq. NaOH. The pH fluctuated between 9–12. During this time the temperature reached 97° C. The total cooking time was 3 hours. The resulting dark brown mixture was then cooled and subjected to the known settling/decantation routine. The routine was repeated until all the loose, free-floating pulp was discarded. After the last decantation, the stone cells were washed first with isopropyl alcohol, followed by a wash with acetone to facilitate their drying in an oven set at 40° C. The dried sand-colored stone cells were free of pulp, and were free flowing.

Example 7

Enzyme Digestion with and without Base Heating

Into a 1000 mL beaker (placed on a magnetic stirrer/hotplate) was added 260 g of a pear puree (made by the same procedure described in Example 1) and enough de-ionized water to fill to the 450 mL mark. The puree was magnetically stirred and warmed to about 53° C., at which time a buffer system was added consisting of 5.40 g of diammonium citrate and 0.70 g of citric acid. The buffer was allowed to dissolve for about 40 minutes. To this mixture was then added 1.30 g of enzyme blend Macer8™ FJ and 1.30 g of enzyme blend Depol™ 670L, both from Biocatalysts Limited. The pH of the mixture was 4–5. The mixture was then digested with continuous stirring for 16 hours in the temperature range of 51–55° C. The mixture was then split into two approximately equal portions. A portion of 212 g was worked up by the usual settling/decantation technique. At the beginning of this procedure, samples of the decantate were checked for clarity. They were cloudy and showed a significant amount of floating undissolved pulp containing entrapped stone cells, which had to be discarded. The stone cells which settled well were isolated by the settling/decantation routine, followed by alcohol/acetone washings, and ultimately dried at 40° C. The remaining portion of the digested mixture was subjected to a simmering under basic conditions by adding, incrementally, a total of 29.0 g of a 50% solution of NaOH to keep the pH at about 11. The mixture was kept between 90–95° C. while continuously stirring for 3 hours. The resulting brown-colored mixture was then diluted with de-ionized water to isolate the stone cells by repeating the familiar settling/decantation routine. At the beginning of this procedure, samples of the decantate were checked for clarity. They were brown and completely clear, with virtually no visible pulp fibers. After the last decantation, the stone cells were washed first with isopropyl alcohol, followed by a wash with acetone, to facilitate their drying in an oven at 40° C. The dried dark beige-colored stone cells were free of pulp, and were free-flowing. This Example shows that it is advantageous to use the enzyme treatment together with the base treatment compared to using the enzyme treatment alone.

Example 8

Base Treatment of Pear Stone Cells and Stone Cell Clusters

Into a 1000 mL beaker (placed on a magnetic stirrer/hotplate) was added 400 g of a pear puree (made by the same procedure described in Example 1) and enough de-ionized water to fill to the 550 mL mark. The diluted puree was magnetically stirred and heated to 93° C. To this stirring mixture was then added, incrementally, a total of 38.5 g of a 50% aqueous solution of NaOH to maintain the pH at about 11. The temperature of the mixture was maintained at about 98° C. during a total period of 6 hours. The resulting dark brown mixture was then split into two equal portions. One portion was cooled with the addition of de-ionized water to isolate the stone cells by repeating the familiar settling/decantation routine. At the beginning of this procedure, samples of the decantate were checked for clarity. They were mostly transparent although some floating undissolved pulp was present. Most of the stone cells had some pulp attached to them, but they settled well. The second portion of the reaction mixture was allowed to continue stirring at room temperature for a total of 65 hours. It was then worked up by the usual settling/decantation technique. At the beginning of this procedure, samples of the decantate were checked for clarity. They were mostly transparent although some floating undissolved pulp was present. Most of the stone cells had some pulp attached to them, but they settled well. Since the stone cells of both fractions had about the same amount of attached fibrous pulp, the fractions were merged into one sample for a subsequent enzyme digestion.

Example 9

Enzyme Treatment of Base-Treated Stone Cells

Into a 1000 mL beaker was added the stone cells of Example 8 and sufficient de-ionized water to fill to 450 mL. To this mixture was added 0.40 g citric acid, and 5.40 g of diammonium citrate. The mixture was heated to 53° C. To this mixture was then added 1.30 g of enzyme blend Macer8™ FJ and 1.30 g of enzyme blend Depol™ 670L, both from Biocatalysts Limited. The mixture was then digested with continuous stirring for 16 hours in the temperature range of 51–55° C. At the conclusion of the digestion the stone cells were subjected to the known settling/decantation routine. The routine was repeated until all the loose, free-floating pulp was discarded. After final washings with isopropanol/acetone, the stone cells were dried at 40° C. The resulting beige stone cells were free of attached pulp fibers, and free-flowing. This example demonstrates that the base treatment can be used before the enzyme treatment however this is not preferred since the base must be substantially removed from the stone cells in order to provide an acidic environment in which the enzyme digestion is effective.

Although particular embodiments of this invention have been disclosed herein for purposes of explanation, further modifications or variations thereof will be apparent to those skilled in the art to which this invention pertains. Further, although certain fruits have been disclosed as being exemplary, the present invention applies to all stone cell-containing fruit. Further, although certain processes have been described by a number of steps in a particular order, the present invention is not limited to any particular order. Thus, the scope of the present invention is meant to be defined only by the appended claims.

What is claimed is:

1. A method for the isolation of stone cells from a fruit, the method comprising:
   providing a puree of a stone cell-containing fruit;
   treating the fruit puree to provide a chemically induced separation of stone cells and stone cell clusters from the pulp of the fruit, wherein said treating step comprises providing a basic compound to the fruit puree to provide a highly basic environment and heating the fruit puree in the highly basic environment;
   washing the stone cells and stone cell clusters to remove any remaining fruit pulp;
   and drying the washed stone cell clusters.

2. The method of claim 1, wherein the fruit is selected from the group consisting of pear, quince, guava, and sapota.

3. The method of claim 1, wherein the basic compound is sodium hydroxide.

4. The method of claim 1, wherein the washing step includes washing the stone cells with isopropyl alcohol.

5. The method of claim 1, wherein the treating step further comprises providing a buffer system to the fruit puree before the addition of the basic compound.

6. The method of claim 5, wherein the buffer system comprises citric acid and diammonium citrate.

7. The method of claim 5, wherein the treating step further comprises providing at least one enzyme to the fruit puree before the addition of the basic compound.

8. The method of claim 7, wherein the at least one enzyme is a pectinase.

9. The method of claim 1, wherein the washing step comprises providing a wash water to the stone cells and decanting off the wash water.

10. The method of claim 9, wherein the washing step further comprises washing the stone cells with isopropyl alcohol.

11. A method for forming a stone cell powder, the method comprising:
   providing a puree of a stone cell-containing fruit;
   providing a basic compound to the fruit puree to form a mixture;
   heating the mixture to provide a chemically induced separation of stone cells and stone cell clusters from the pulp of the fruit;
   washing the stone cells and stone cell clusters to remove any remaining fruit pulp; and
   drying the washed stone cells and stone cell clusters to provide a free-flowing stone cell powder.

12. The method of claim 11, further comprising providing at least one enzyme to the fruit puree.

13. The method of claim 12, wherein the step of providing at least one enzyme takes place before the step of providing a basic compound.

14. The method of claim 12, wherein the step of providing at least one enzyme takes place after the step of providing a basic compound.

15. A method of forming an exfoliating cream, the method comprising:
   providing a puree of a stone cell-containing fruit;
   treating the fruit puree to provide a chemically induced separation of stone cells and stone cell clusters from the pulp of the fruit, wherein said treating step comprises providing a basic compound to the fruit puree to provide a highly basic environment and heating the fruit puree in the highly basic environment;
   washing the stone cells and stone cell clusters to remove any remaining fruit pulp;
   drying the washed stone cells and stone cell clusters to provide a free-flowing stone cell powder;
   and providing the stone cell powder to a base cream.

16. The method of claim 15, wherein the treating step further comprises providing a buffer system to the fruit puree before the addition of the basic compound.

17. The method of claim 16, wherein the treating step further comprises providing at least one enzyme to the fruit puree before the addition of the basic compound.

18. The method of claim 17, wherein the at least one enzyme is a pectinase.

* * * * *